(12) United States Patent
Sham et al.

(10) Patent No.: US 8,768,454 B2
(45) Date of Patent: *Jul. 1, 2014

(54) ELECTROMAGNETIC THERMAL THERAPY

(75) Inventors: Kin-Joe Sham, Shoreview, MN (US); Jared Jon Savela, Little Canada, MN (US)

(73) Assignee: OrthoCor Medical, Inc., Minneapolis, MN (US)

(*) Notice: Subject to any disclaimer, the term of this patent is extended or adjusted under 35 U.S.C. 154(b) by 731 days.

This patent is subject to a terminal disclaimer.

(21) Appl. No.: 12/831,779

(22) Filed: Jul. 7, 2010

(65) Prior Publication Data

US 2011/0004261 A1    Jan. 6, 2011

Related U.S. Application Data

(63) Continuation-in-part of application No. 12/104,007, filed on Apr. 16, 2008, now Pat. No. 7,783,348.

(60) Provisional application No. 60/927,354, filed on May 3, 2007, provisional application No. 60/983,653, filed on Oct. 30, 2007.

(51) Int. Cl.
*A61N 1/18* (2006.01)
*A61F 5/00* (2006.01)

(52) U.S. Cl.
USPC ..................................... 607/3; 607/46; 602/2

(58) Field of Classification Search
USPC ............ 600/14, 15; 607/2, 3, 50, 51, 108, 46, 607/49; 602/2, 7, 26
See application file for complete search history.

(56) References Cited

U.S. PATENT DOCUMENTS

| | | | |
|---|---|---|---|
| 4,240,445 A | 12/1980 | Iskander et al. | |
| 4,256,116 A | 3/1981 | Meretsky et al. | |
| 4,412,540 A | 11/1983 | Bentall | |
| 4,548,208 A * | 10/1985 | Niemi | 600/14 |
| 4,674,482 A | 6/1987 | Waltonen et al. | |
| 4,727,857 A | 3/1988 | Horl | |
| 4,757,804 A | 7/1988 | Griffith et al. | |
| 4,886,063 A | 12/1989 | Crews | |
| 4,989,604 A | 2/1991 | Fang | |
| 5,000,178 A | 3/1991 | Griffith | |

(Continued)

FOREIGN PATENT DOCUMENTS

| | | |
|---|---|---|
| WO | WO-2004069128 A1 | 8/2004 |
| WO | WO-2006096698 A2 | 9/2006 |

(Continued)

OTHER PUBLICATIONS

"U.S. Appl. No. 12/104,007 Notice of Allowance mailed Jun. 30, 2010", 12 pgs.

(Continued)

*Primary Examiner* — Eric D. Bertram
*Assistant Examiner* — Pamela M Bays
(74) *Attorney, Agent, or Firm* — Schwegman Lundberg & Woessner, P.A.

(57) ABSTRACT

A portable, non-invasive device for providing therapeutic treatment to a joint to promote healing of the joint includes a cuff positionable around the joint. The cuff includes an electromagnetic stimulator configured to provide an electromagnetic field within the joint and a single-use thermal exchange component configured to provide temperature-based therapy to the joint.

17 Claims, 11 Drawing Sheets

(56) References Cited

U.S. PATENT DOCUMENTS

| | | |
|---|---|---|
| 5,014,699 A | 5/1991 | Pollack et al. |
| 5,179,942 A * | 1/1993 | Drulias et al. ............. 128/101.1 |
| 5,181,902 A | 1/1993 | Erickson et al. |
| 5,314,401 A | 5/1994 | Tepper |
| 5,336,255 A | 8/1994 | Kanare et al. |
| 5,401,233 A | 3/1995 | Erickson et al. |
| 5,411,542 A | 5/1995 | Jensen |
| 5,478,303 A | 12/1995 | Foley-Nolan et al. |
| 5,487,759 A | 1/1996 | Bastyr et al. |
| 5,578,065 A | 11/1996 | Hattori et al. |
| 5,584,863 A | 12/1996 | Rauch et al. |
| 5,718,721 A | 2/1998 | Ross |
| 5,723,001 A | 3/1998 | Pilla et al. |
| 5,743,844 A | 4/1998 | Tepper et al. |
| 5,792,213 A | 8/1998 | Bowen |
| 5,860,945 A | 1/1999 | Cramer et al. |
| 5,904,710 A * | 5/1999 | Davis et al. ................... 607/108 |
| 5,922,012 A | 7/1999 | Sakano |
| 5,947,913 A | 9/1999 | Palumbo |
| 5,951,459 A | 9/1999 | Blackwell |
| 6,024,691 A | 2/2000 | Tepper et al. |
| 6,042,531 A | 3/2000 | Holcomb |
| 6,096,067 A | 8/2000 | Cramer et al. |
| 6,129,659 A | 10/2000 | Wilk |
| 6,132,362 A | 10/2000 | Tepper et al. |
| 6,186,941 B1 | 2/2001 | Blackwell |
| 6,200,259 B1 | 3/2001 | March |
| 6,213,934 B1 | 4/2001 | Bianco et al. |
| 6,228,108 B1 | 5/2001 | Lamb et al. |
| 6,261,221 B1 | 7/2001 | Tepper et al. |
| 6,275,737 B1 | 8/2001 | Mann |
| 6,334,069 B1 * | 12/2001 | George et al. ..................... 607/2 |
| 6,353,763 B1 | 3/2002 | George et al. |
| 6,436,020 B1 | 8/2002 | Weingand |
| 6,443,883 B1 | 9/2002 | Ostrow et al. |
| 6,445,955 B1 * | 9/2002 | Michelson et al. ............. 607/46 |
| 6,463,336 B1 | 10/2002 | Mawhinney |
| 6,465,709 B1 | 10/2002 | Sun et al. |
| 6,506,403 B1 | 1/2003 | Yu |
| 6,551,233 B2 | 4/2003 | Perreault et al. |
| 6,561,968 B1 | 5/2003 | Dissing et al. |
| 6,589,159 B2 | 7/2003 | Paturu |
| 6,592,509 B1 | 7/2003 | Hunter, Jr. |
| 6,602,213 B2 | 8/2003 | Figley |
| 6,606,519 B2 | 8/2003 | Powell |
| 6,641,520 B2 | 11/2003 | Bailey et al. |
| 6,652,446 B1 * | 11/2003 | Bove et al. ....................... 600/15 |
| 6,675,047 B1 | 1/2004 | Konoplev et al. |
| 6,678,562 B1 | 1/2004 | Tepper et al. |
| 6,701,185 B2 | 3/2004 | Burnett et al. |
| 6,839,595 B2 | 1/2005 | Tepper et al. |
| 6,875,188 B2 | 4/2005 | Chiang |
| 6,955,642 B1 | 10/2005 | Simon |
| 7,008,369 B2 | 3/2006 | Cuppen |
| 7,022,506 B2 | 4/2006 | Brighton et al. |
| 7,087,076 B2 | 8/2006 | Purcell |
| 7,130,692 B2 | 10/2006 | Brighton et al. |
| 7,175,587 B2 | 2/2007 | Gordon et al. |
| 7,215,995 B2 | 5/2007 | Brighton et al. |
| 7,336,993 B1 | 2/2008 | Szeles |
| 7,551,957 B2 | 6/2009 | Whelan et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,783,348 B2 | 8/2010 | Gill et al. |
| 2001/0018605 A1 | 8/2001 | Helming |
| 2002/0143373 A1 | 10/2002 | Courtnage et al. |
| 2004/0010178 A1 | 1/2004 | Buckner |
| 2004/0044384 A1 * | 3/2004 | Leber et al. ..................... 607/88 |
| 2004/0097855 A1 * | 5/2004 | Page et al. ......................... 602/7 |
| 2004/0097856 A1 * | 5/2004 | Cipra et al. ....................... 602/7 |
| 2004/0176803 A1 | 9/2004 | Whelan et al. |
| 2004/0176805 A1 | 9/2004 | Whelan et al. |
| 2004/0176806 A1 | 9/2004 | Markoll |
| 2005/0049653 A1 | 3/2005 | Wang |
| 2005/0087194 A1 | 4/2005 | Scott |
| 2006/0190043 A1 | 8/2006 | Brighton et al. |
| 2007/0106354 A1 * | 5/2007 | Carstens ....................... 607/112 |
| 2007/0167990 A1 | 7/2007 | Mangrum et al. |
| 2008/0039810 A1 | 2/2008 | Lee et al. |
| 2008/0132971 A1 | 6/2008 | Pille et al. |
| 2008/0288035 A1 | 11/2008 | Gill et al. |
| 2010/0222631 A1 | 9/2010 | Pilla |
| 2011/0065977 A1 | 3/2011 | Sham et al. |
| 2012/0330090 A1 | 12/2012 | Sham et al. |

FOREIGN PATENT DOCUMENTS

| | | |
|---|---|---|
| WO | WO-2006115119 A1 | 11/2006 |
| WO | WO-2008137319 A1 | 11/2008 |
| WO | WO-2012005766 A1 | 1/2012 |

OTHER PUBLICATIONS

"U.S. Appl. No. 12/104,007, Response filed Mar. 22, 2010 to Non Final Office Action maield Oct. 21, 2009", 18 pgs.

"CDRH Document Imaging System: Folder K903675", (Nov. 1992), 77 pgs.

"International Search Report and Written Opinion of International Application No. PCT/US2008/061214, mailed Jul. 8, 2008", 14 pgs.

"Ivivi SofPulse: Premarket Notification [501(k)] Summary", *Ivivi Technologies Inc.*, (Dec. 2008) 5 pgs.

"OrthoCor Active Knee System: Premarket Notification [501(k)] Summary", *Orthocor Medical, Inc.*, (Dec. 2009), 5 pgs.

Fini, et al., "Effects of pulsed electromagnetic fields on articular hyaline cartilage: review of experimental and clinical studies", *Biomedicine & Pharmacotherapy 59*, (Feb. 2005), 388-394.

Sutbeyaz, et al., "The effect of pulsed electromagnetic fields in the treatment of cervical osteoarthritis: a randomized, double-blink, sham-controlled trail", *Rheumatol Int*, 26, (Jan. 2006), 320-324.

International Application Serial No. PCT/US2011/001187, International Preliminary Report on Patentability mailed Jan. 17, 2013, 8 pgs.

International Application Serial No. PCT/US2011/001187, Search Report mailed Sep. 23, 2011, 4 pgs.

International Application Serial No. PCT/US2011/001187, Written Report mailed Sep. 23, 2011, 7 pgs.

Pilla, A. A, et al., "EMF signals and ion/ligand binding kinetics: prediction of bioeffective waveform parameters", Bioelectrochemistry and Bioenergetics, 48(1), (Feb. 1999), 27-34.

* cited by examiner

ELECTROMAGNETIC THERMAL THERAPY

CLAIM OF PRIORITY

This application is a continuation-in-part of commonly assigned Gill et al. U.S. patent application Ser. No. 12/104,007, now U.S. Pat. No. 7,783,348, entitled "STIMULATION DEVICE FOR TREATING OSTEOARTHRITIS," filed on Apr. 16, 2008, which claims priority to Gill et al. U.S. Patent Application Ser. No. 60/927,354, entitled "STIMULATION DEVICE FOR TREATING OSTEOARTHRITIS," filed on May 3, 2007, and to Gill et al. U.S. Patent Application Ser. No. 60/983,653, entitled "STIMULATION DEVICE FOR TREATING OSTEOARTHRITIS," filed on Oct. 30, 2007, the benefit of priority of each of which is claimed hereby, and each of which are incorporated by reference herein in its entirety.

BACKGROUND

Osteoarthritis, also known as degenerative joint disease, is characterized by gradual loss of hyaline cartilage and, in extreme cases, cyst formation in and deformation of the subchondral bone. The hyaline cartilage lines the articular surfaces of the knee and provides cushion and lubrication for the joint. During osteoarthritis, the extra-cellular matrix of the cartilage is worn down at a greater rate than it is being synthesized, leading to a net reduction in the overall amount of cartilage at the articular surfaces of the knee. As the cartilage breaks down, symptoms such as pain, swelling, tenderness, stiffness, and eventual muscle atrophy are manifested. Chondrocytes, the cellular component of hyaline cartilage that is responsible for matrix synthesis and turnover, are also depleted, thus resulting in an inability to naturally recover from this disease. Additionally, cells present in osteoarthritic joints release catabolic cytokines and enzymes that suppress collagen synthesis.

To date, conventional therapies for osteoarthritis have aimed at reducing pain and the progression of joint damage in order to minimize disability and maximize quality of life. The current algorithm for the management of osteoarthritis includes diagnosing the disease, modifying patient activity, prescribing anti-inflammatory medications, injecting steroids into the knee, and as a last resort, surgery. Although this regimen does provide some benefit, it is by no means a cure all for patients with osteoarthritis.

Aside from the conventional therapies, there are currently a number of alternative therapies that may be used to treat osteoarthritis. Three of the forerunners in the non-invasive alternative therapy field include electric, static magnetic, and electromagnetic stimulation.

Electrical stimulation, such as transcutaneous electrical nerve stimulation (TENS), delivers mild electrical impulses across the skin and into regional nerves. In patients having osteoarthritis, pain impulses are transmitted to the spinal cord through small cutaneous fibers. TENS acts to stimulate large cutaneous fibers that subsequently transmit a faster impulse via C-fibers to inhibit pain signals from the small fibers. It is in this way that TENS masks the pain normally experienced by patients having osteoarthritis. It is also thought that TENS incites the secretion of endogenous opiates, the body's natural pain killers, further reducing the pain experienced by patients with osteoarthritis.

Static magnetic stimulation has also been shown to provide medically relevant benefits. Various experiments designed to induce osteoporosis, fracture, and synovitis in animals have demonstrated faster bone repair, increased bone density, and decreased joint inflammation following magnetic treatments. It is thought that magnets can affect biological processes by: decreasing the firing rate of chronic pain neurons; modifying the rate of enzyme-mediated reactions; modulating intracellular signaling by affecting the functioning of calcium channels in the cell membranes; and enhancing blood flow. All of the above may provide some therapeutic benefit with respect to the symptoms of osteoarthritis.

Additionally, electromagnetic stimulation, a modality that generates a magnetic field by sending current through a coil, may also provide medical benefits for the treatment of osteoarthritis. It has been observed that physical stress on bone causes the appearance of tiny electric currents (piezoelectric potentials) that are thought to be the mechanism of transduction of the physical stresses into a signal that promotes bone formation. In particular, studies of electrical phenomena in cartilage have demonstrated a mechanical-electrical transduction mechanism resembling those described in bone, appearing when cartilage is mechanically compressed. Generating currents within cartilage is thought to stimulate chondrocyte activity, thus promoting the synthesis of cartilage. New cartilage synthesis may work to combat the degeneration seen in osteoarthritis and therefore alleviate the symptoms of osteoarthritis.

Thus, there is a need for an improved device and method to treat osteoarthritis.

Overview

In various embodiments disclosed herein, devices or methods for the treatment of osteoarthritis are disclosed. More particularly, certain embodiments relate to portable, disposable pulsed electromagnetic field (PEMF) stimulation and thermal therapy devices for treating osteoarthritis and their methods of use.

A portable, non-invasive device comprised of a multiple usage cuff and two single-use therapy units is designed to provide Electro-Magnetic Thermal Therapy ($EMT^2$) for treating knee osteoarthritis. The $EMT^2$ provides both transcutaneous pulsed electromagnetic field stimulation and thermal therapy. For purposes of this application, it is understood that "thermal therapy" means any therapy that provides for application of heat or cold for purposes of treatment. The $EMT^2$ is designed to alleviate pain and increase range of motion without requiring direct skin contact to the afflicted joint. The single-use therapy units offer heat or cooling and PEMF stimulation when inserted into the cuff, which provides the power and control for the coils. The cuff may contain a rechargeable power source capable of delivering a recommended amount of therapy and the coils for delivering the PEMF stimulation. The cuff may be fastened to the knee in a manner that directs the therapy to the medial and lateral areas of the joint. Furthermore, the cuff may be designed such that it is aesthetically pleasing and comfortable to wear during daily activities either over or underneath clothing, thereby increasing patient compliance.

The basic principle behind the concept of electromagnetic stimulation is that passing an electric current through a coil winding structure will generate an electromagnetic field. The electromagnetic field can, in turn, generate a current in any conductive material, such as nerves or other body tissues, within this field. The electromagnetically induced electric field created by properly oriented pulsed electromagnetic stimulation thus accomplishes the result of transferring charge to cells of the body. This induced current can lead to nerve firing, muscle contraction, stimulation of cell signaling pathways causing cell growth, and a number of other effects.

In contrast to applications of electrical stimulation, pulsed electromagnetic stimulation does not require direct skin contact to induce nerve excitation. As a result, significantly higher levels of directed stimulation can be achieved through pulsed electromagnetic stimulation without the adverse effects of other technologies.

Thus, the $EMT^2$ devices and methods disclosed herein are designed with a powerful electromagnetic stimulating means created for the purpose of stimulating nerve, muscle, and/or other body tissues. Previous clinical studies have shown a high correlation between low-frequency PEMF and new cartilage growth for treating osteoarthritis. The inventive device provides an easy-to-use, portable system that may have applications within a host of clinical and home health applications.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A device for providing therapeutic treatment to a body part such as a joint to promote healing of the body part comprises a signal generator for generating a pulsed electromagnetic field based upon a selected treatment mode, a controller for storing the treatment mode and communicating the treatment mode to the signal generator, a heat source configured to provide thermal therapy to the body part, and monitoring means for monitoring the electromagnetic field generated by the electromagnetic stimulating means. The device may also include telemetry means in communication with the monitoring means for remotely accessing the controller to modify the treatment mode. The device can also be disposable.

Figure 1:
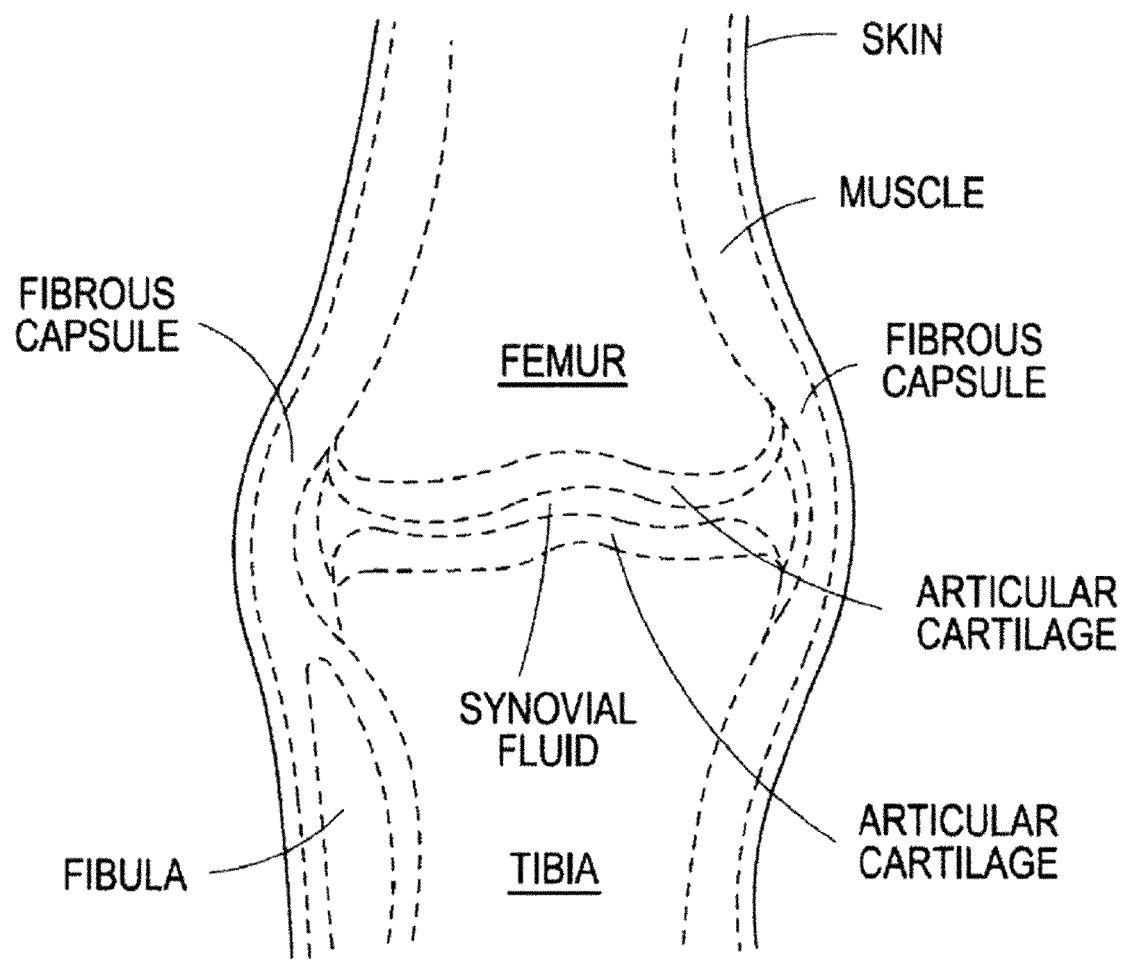
FIG. 1 is a diagram illustrating a typical human knee joint model.

FIG. 1 is a diagram illustrating a typical human knee joint model. As shown in FIG. 1, the typical human knee joint includes a compartment filled with synovial fluid that is bounded by articular cartilage on the ends of the femur and tibia, respectively, and fibrous capsules. In accordance with one embodiment of the devices and methods discussed herein, osteoarthritis in the knee joint may be treated by the application of heat or cold and specific and selective electromagnetic fields via coils positioned adjacent to the knee joint. As will be discussed in more detail to follow, a signal generator means may provide the appropriate signals to the coils for generating the specific and selective electromagnetic fields. The specific and selective electromagnetic field needed to treat osteoarthritis in the knee joint may be calculated, and varies depending upon, among other factors, the dimensions of the tibia and femur and the severity of the symptoms. Furthermore, a heating or cooling source may also be positioned adjacent to the knee joint to relieve pain, reduce patient discomfort, and increase range of motion. The heating or cooling source can also be referred to as a "thermal exchange component," which, for purposes of the instant application, means any component or device that can be used to apply heat (or any temperature that is higher than the patient's body temperature or the ambient temperature) or cold (or any temperature that is lower than the patient's body temperature or the ambient temperature).

More particularly, the implementations discussed herein relate to devices and methods for generating both (1) heat or cold, and (2) selective pulsed electromagnetic fields for the treatment of diseased tissue in a joint, such as a knee joint. The devices, which may be designed in numerous forms such as a knee brace or a small dermal patch, preferably offer transcutaneous stimulation for treating osteoarthritis. The devices may be designed to provide stimulation directly to the afflicted joint to alleviate pain and increase range of motion.

As will be discussed in further detail in subsequent paragraphs, the various $EMT^2$ stimulation device embodiments may be designed to attach to a patient for a prolonged period of time while having little disruption to daily activities and minimal skin irritation. In addition, the stimulation devices may be designed such that it is aesthetically pleasing and comfortable to wear. As a result of these and other design characteristics, patient refusal of treatment due to discomfort (i.e., patient "non-compliance") may be minimized.

Pulsed electromagnetic fields generate small, induced currents (Faraday currents) in the highly conductive extracellular fluid, which thereby mimics endogeneous electrical currents. The endogeneous electrical currents are due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials serve a purpose in cartilage similar to that in bone, and, along with mechanical strain, lead to signal transduction that is capable of stimulating chondrocyte synthesis of matrix components.

In contrast to direct currents, PEMFs are able to penetrate cell membranes and either stimulate them or directly affect intracellular organelles. As a result, the effect of PEMFs on extracellular matrices includes increased synthesis of cartilage molecules, thereby enabling a "remodeling" of the knee joint.

Figure 2:
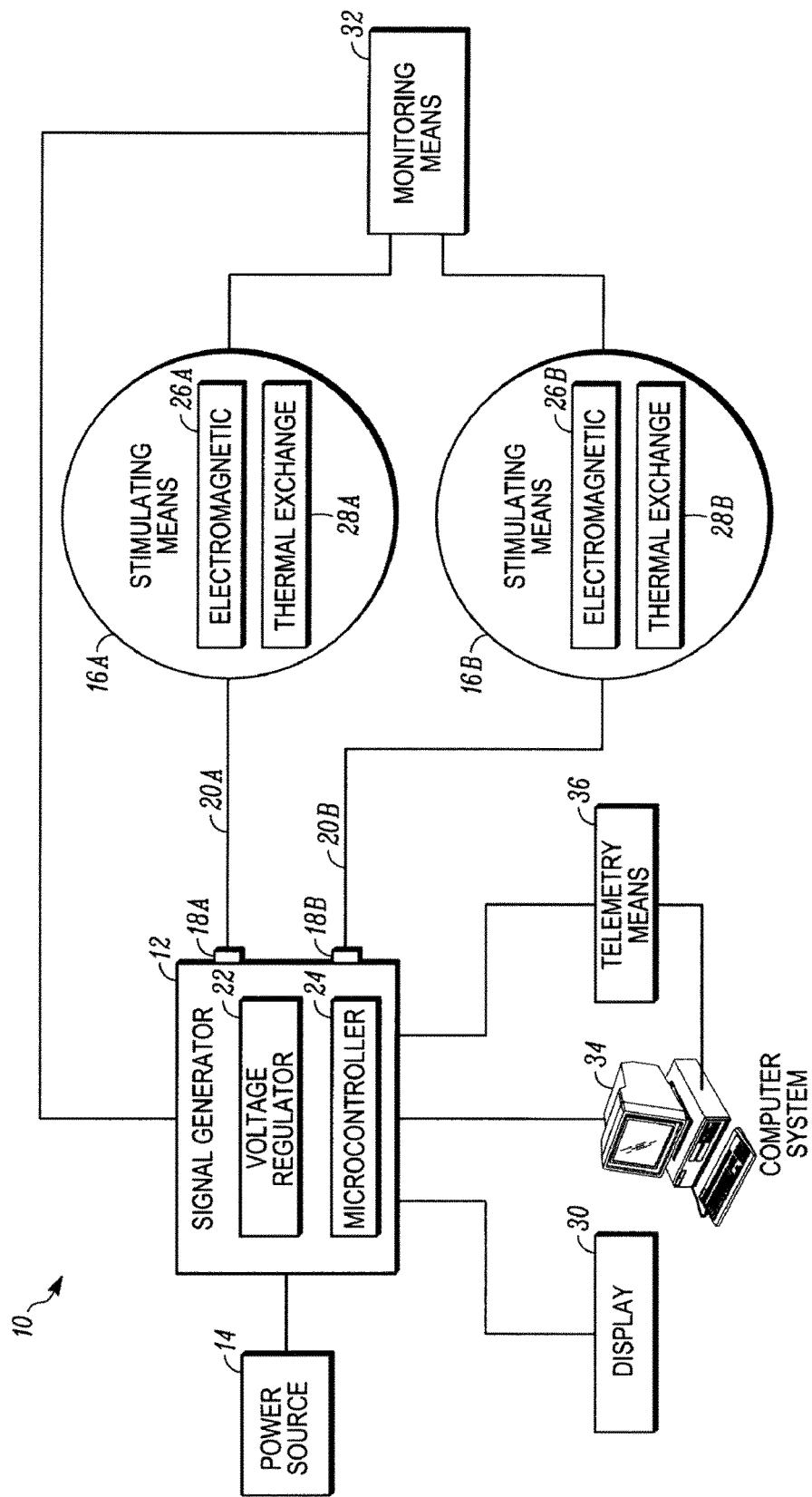
FIG. 2 is a block diagram illustrating a stimulation device for treating osteoarthritis in the knee according to one embodiment.

FIG. 2 is a block diagram illustrating $EMT^2$ stimulation device 10 for treating osteoarthritis in the knee according to one embodiment. This device embodiment 10 has a signal generator 12, power source 14, first stimulating means 16A, and second stimulating means 16B. First stimulating means 16A is coupled to first output 18A of signal generator 12 via first signal line 20A. Similarly, second stimulating means 16B is coupled to second output 18B of signal generator 12 via second signal line 20B. In various embodiments, the first stimulating means 16A has either or both of an electromagnetic stimulating means 26A and a thermal exchange component 28A and the second stimulating means 16B has either or both of an electromagnetic stimulating means 26B and a thermal exchange component 28B.

First and second signal lines 20A and 20B are configured to deliver the signals generated by signal generator 12 to create the appropriate therapeutic stimulation via first and second stimulating means 16A and 16B. First and second signal lines 20A and 20B may be "wired," such as with coaxial cable. Alternatively, a "wireless" connection means, such as Bluetooth, may be used.

Although stimulation device 10 is shown as having two output ports 18A and 18B for simultaneously and independently delivering output signals (either the same or different signals) to two stimulating means 16A and 16B, one skilled in the art will appreciate that the number of output ports and stimulating means may be varied without departing from the intended scope of the implementations disclosed herein. Thus, embodiments of device 10 that include any number of stimulating means are contemplated. For example, in one alternative embodiment, the device 10 can have one stimulating means.

Power source 14, which may be, for example, a lithium battery pack, is provided for delivering a current input to signal generator 12. While shown in FIG. 2 as a remote unit, power source 14 may be incorporated as part of or housed together with signal generator 12. Since the embodiments may be designed with low power requirements, power source 14 may be one capable of providing an average power input of less than about 300 mW per session. As a result, power source 14 is generally small and lightweight. In an alternative embodiment, the device 10 has two power sources—one to supply power to the signal generator and another to supply power to create the thermal exchange.

As shown in FIG. 2, signal generator 12 may include voltage regulator 22 and microcontroller 24. Furthermore, first stimulating means 16A may include first electromagnetic stimulating means 26A and first thermal exchange component 28A, while second stimulating means 16B may include second electromagnetic stimulating means 26B and second thermal exchange component 28B. In one embodiment, the first and second electromagnetic stimulating means 26A, 26B are first and second coils 26A, 26B. Voltage regulator 22 may be used to provide various required supply voltages to first and second electromagnetic stimulating means 26A and 26B. First and second electromagnetic stimulating means 26A and 26B may be triggered by microcontroller 24, which may be designed to generate accurate pulses at a particular triggering and switching frequency. Output signals are delivered from microcontroller 24 to first and second stimulating means 16A and 16B, each of which is individually responsive to the signals to create a pulsed electromagnetic field.

As shown in FIG. 2, alternative embodiments of the device 10 may further include display 30 and monitoring means 32. Display 30 may be designed to display many different treatment parameters, including but not limited to a treatment mode, a power level, and an amount of time remaining in a treatment session.

Monitoring means 32 may be designed for monitoring one or more of the output conditions of stimulation device 10. In particular, monitoring means 32 may be configured to ensure that accurate treatment dosages are delivered through first and second stimulating means 16A and 16B to the patient's knee. One condition that may be monitored by monitoring means 32 is the electromagnetic field generated by first and second coils 26A and 26B. In particular, monitoring means 32 may include circuitry to both detect the strength of the electromagnetic field and adjust the signals delivered to the coils if the sensed field is not in accordance with the desired treatment level. A second condition that may be monitored by monitoring means 32 is tissue temperature generated by first and second thermal exchange component 28A and 28B. If, for example, monitoring means 32 senses a tissue temperature that is out of an acceptable range and poses a danger of injuring tissue around the knee, monitoring means 32 may communicate with the patient through display 30 to instruct removal of device 10 from the patient's knee.

For example, in one embodiment, monitoring means 32 may include a signal detector coupled to first stimulating means 16A and/or second stimulating means 16B for measuring the energy emission from first and second coils 26A and 26B. The signal detector may be designed so as to transmit a feedback signal to signal generator 12 for controlling the energy output. The actual electromagnetic energy field, or treatment dosage, that is transmitted from first and second stimulating means 16A and 16B may be measured directly by embedding the signal strength detector within the stimulating means. The signal level measured by the signal detector may then be sent to signal generator 12, where it may be used as a feedback control signal to control the output signals of the generator. If, at any time, monitoring means 32 detects a field strength outside of the desired range of the treatment mode, display 30 may display an audible, visible, tactile, or other type of alarm to inform the patient and/or physician of a malfunction in the treatment mode. Furthermore, if the measured field strength is at or above a level that poses a risk of danger, the feedback circuit of monitoring means 32 may stop the treatment to ensure that the patient is not harmed. As will be appreciated by one skilled in the art, monitoring means 32 may alternatively or additionally include a temperature sensor and associated feedback control to sense and control tissue temperature around the patient's knee.

As shown in FIG. 2, device 10 may be connected to a computer system 34 to allow the physician to program treatment modes into microcontroller 24. In this manner, the physician retains control over the type of treatment that the patient receives since device 10 may be designed such that only the physician is able to access and modify the programmed treatment modes. Through computer system 34, the physician may also monitor the treatment conditions to ensure that, for example, the correct field strength is being generated.

In order to make treatment with stimulation device 10 more convenient for both the physician and the patient, telemetry means 36 may be incorporated into the device. In general, telemetry allows for the remote measurement and reporting of information of interest to a remote system or operator. In addition, telemetry allows for the remote operation and control of a device by allowing the operator to remotely send instructions to or program the device.

With respect to stimulation device 10, telemetry means 36 enables the physician to remotely monitor the treatment as well as modify the treatment modes programmed into microcontroller 24. In this way, the physician has the ability to control and prescribe treatment modes without the requirement of a face-to-face consultation with the patient, thus making treatment of osteoarthritis more convenient for both the patient and the physician. In one embodiment, telemetry means 36 may operate using wireless communication, such as by utilizing a radio frequency (RF) system to implement the data link between the device and remote system. However, telemetry means 36 may alternatively transfer data over other media, such as a telephone line, a computer network, or via an optical link.

Figure 3:
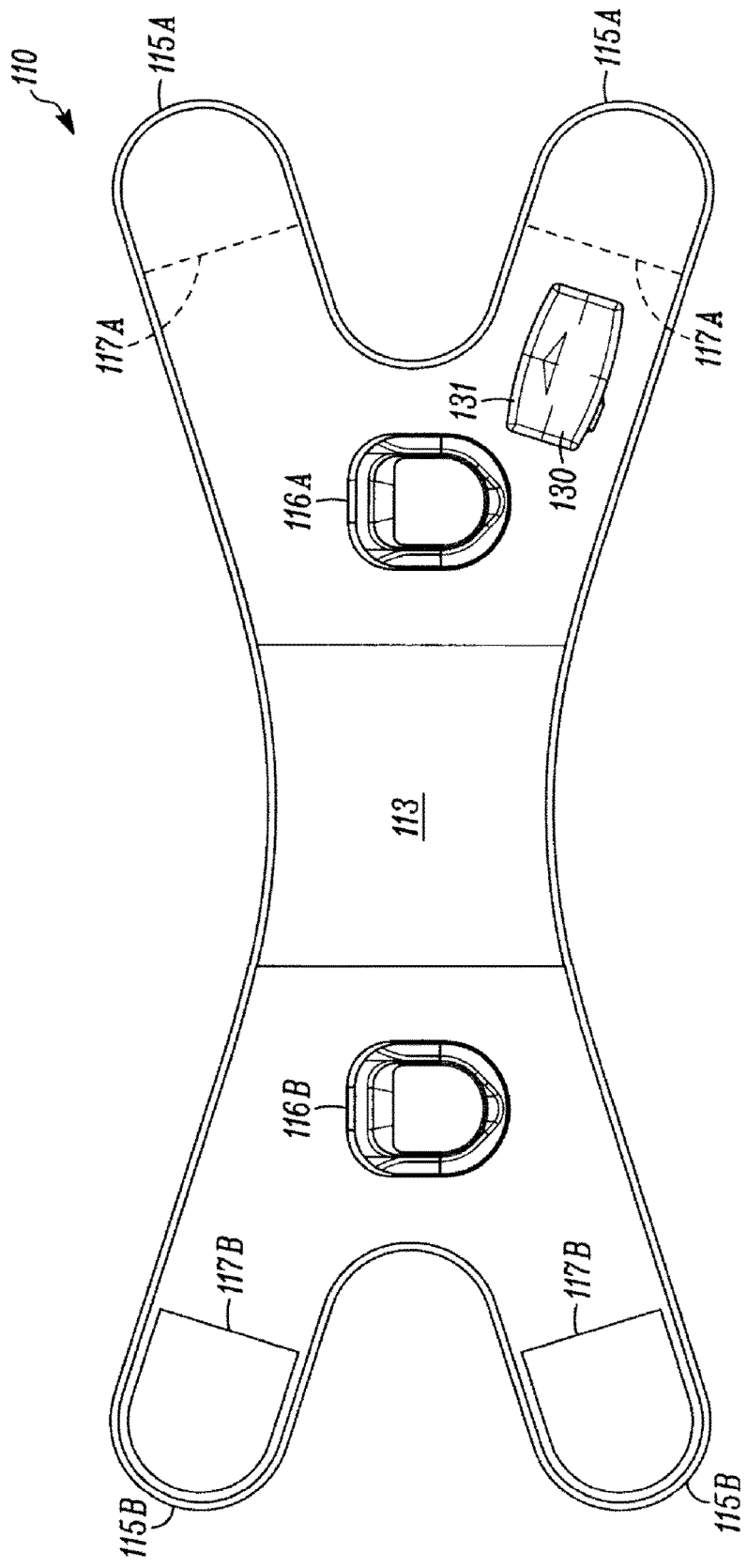
FIG. 3 is a front view of one embodiment of a stimulation device that is securable to a patient's knee for delivery of electromagnetic and thermal therapy.

Now that certain embodiments of the EMT$^2$ stimulation device have been generally described in reference to the block diagram illustration of FIG. 2, one exemplary embodiment of a stimulation device that may be worn by a patient for the treatment of osteoarthritis will be described. In particular, FIG. 3 illustrates a stimulation device 110, which generally includes a knee cuff 111, a housing 131 in which a signal generator and a power source are positioned, a first stimulating means 116A, a second stimulating means 116B, and a fastening means 117. The housing 131 can be positioned anywhere on the cuff 111. The device 110 alternatively also has a display 130 that can display one or more treatment parameters, such as the treatment mode or the amount of treatment time remaining in a therapy session. In the embodiment depicted in FIG. 3, the display 130 is located on the housing 131. Alternatively, the display 130 can be positioned in any location from which the display is visible to the user during use. Stimulation device 110 is a device for providing electromagnetic field stimulation and thermal therapy to a patient's body to promote healing. In particular, stimulation device 110 may provide pulsed electromagnetic field stimulation and thermal therapy (via first and second stimulating means 116A and 116B) to a knee joint suffering from the effects of osteoarthritis to promote healing of the knee. However, one skilled in the art will appreciate that various device embodiments disclosed herein may be useful to provide electromagnetic field stimulation and thermal therapy (EMT$^2$) to various other locations on a patient's body to promote healing or provide a therapeutic effect.

Knee cuff 111 includes main body portion 113, first set of strap members 115A, and second set of strap members 115B. First set of strap members 115A include first fastening members 117A, while second set of strap members 115B include second fastening members 117B. As will be discussed in the following paragraphs, first fastening members 117A are configured to mate with second fastening members 117B in order to removably couple first set of strap members 115A to second set of strap members 115B and thus, to secure knee cuff 111 to the patient's knee.

Figure 4A:
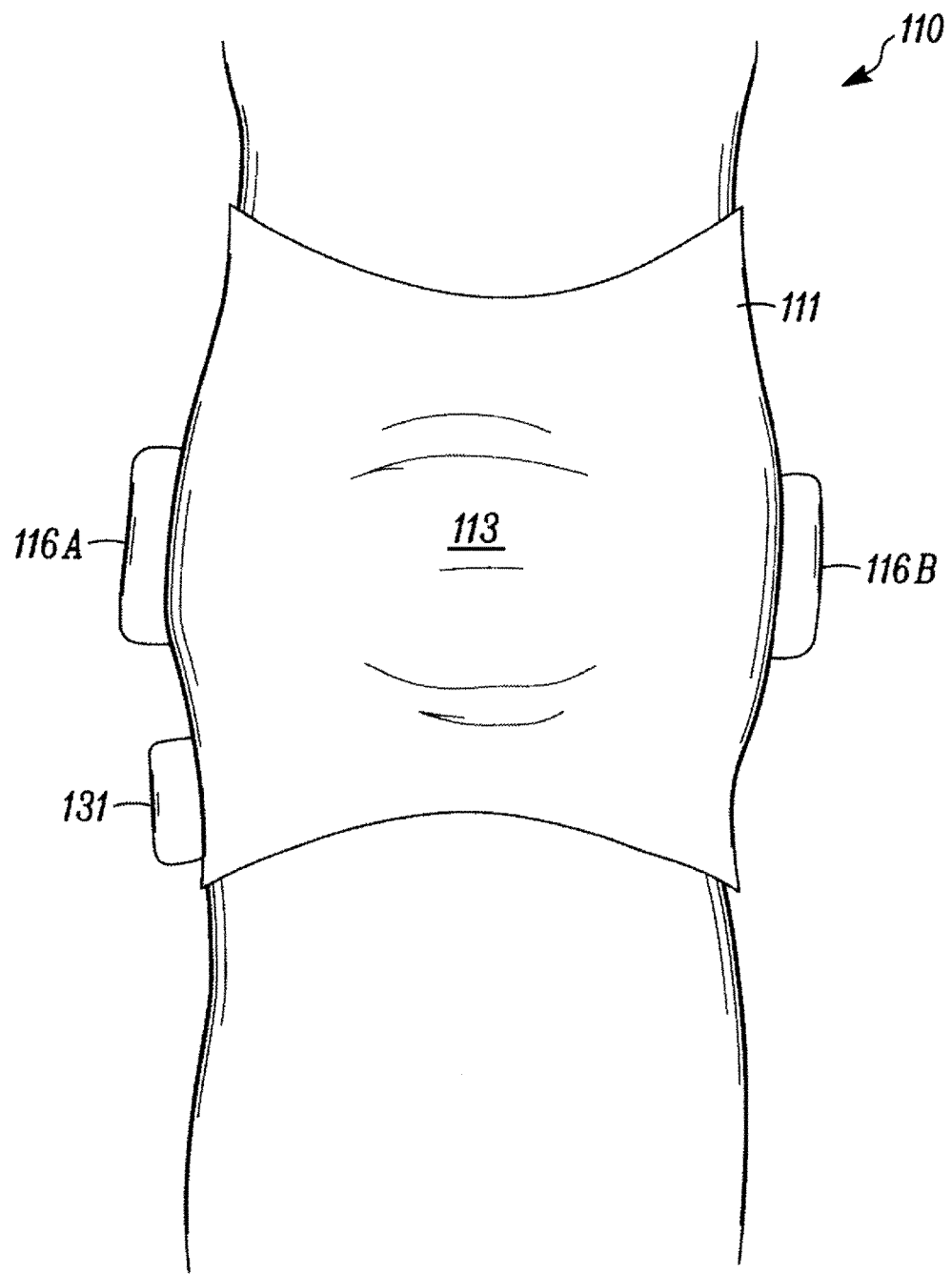
FIGS. 4A and 4B illustrate the stimulation device of FIG. 3 secured to the patient's knee.
Figure 4B:
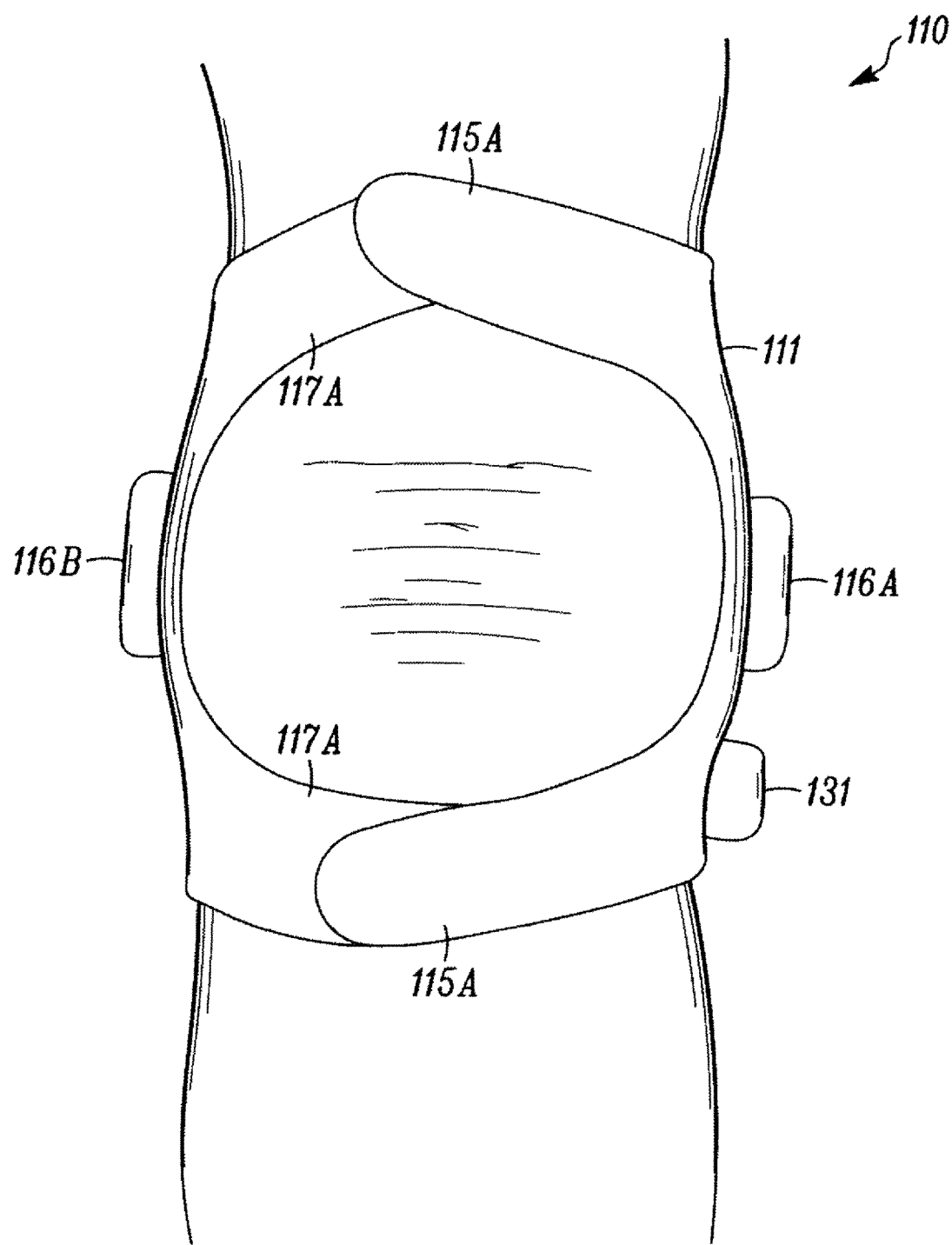

FIGS. 4A and 4B illustrate stimulation device 110 secured to the patient's knee, according to one embodiment. In particular, FIG. 4A illustrates a front side of the patient's knee, while FIG. 4B illustrates a back side of the knee. Knee cuff 111 of stimulation device 110 is wrapped around the knee such that first set of strap members 115A having first fastening members 117A overlap with second set of strap members 115B having second fastening members 117B to secure the cuff at the desired location on the knee. When properly secured to the knee, first stimulation means 116A is positioned at a lateral knee location, while second stimulating means 116B is positioned at a medial knee location. In one embodiment, first fastening members 117A and second fastening members 117B form a hook-and-loop fastening means, such as that commonly known as VELCRO®, wherein first fastening members 117A are the "hook" portions and second fastening members 117B are the "loop" portions. However, other means of fastening may be used including, but not limited to, buckles, snaps, and zippers. In alternate embodiments of knee cuff 111, no fastening means is used. Instead, the fabric forming the wrap is capable of being stretched and is able to hold itself in place due to the elasticity of the wrap.

Figure 5:
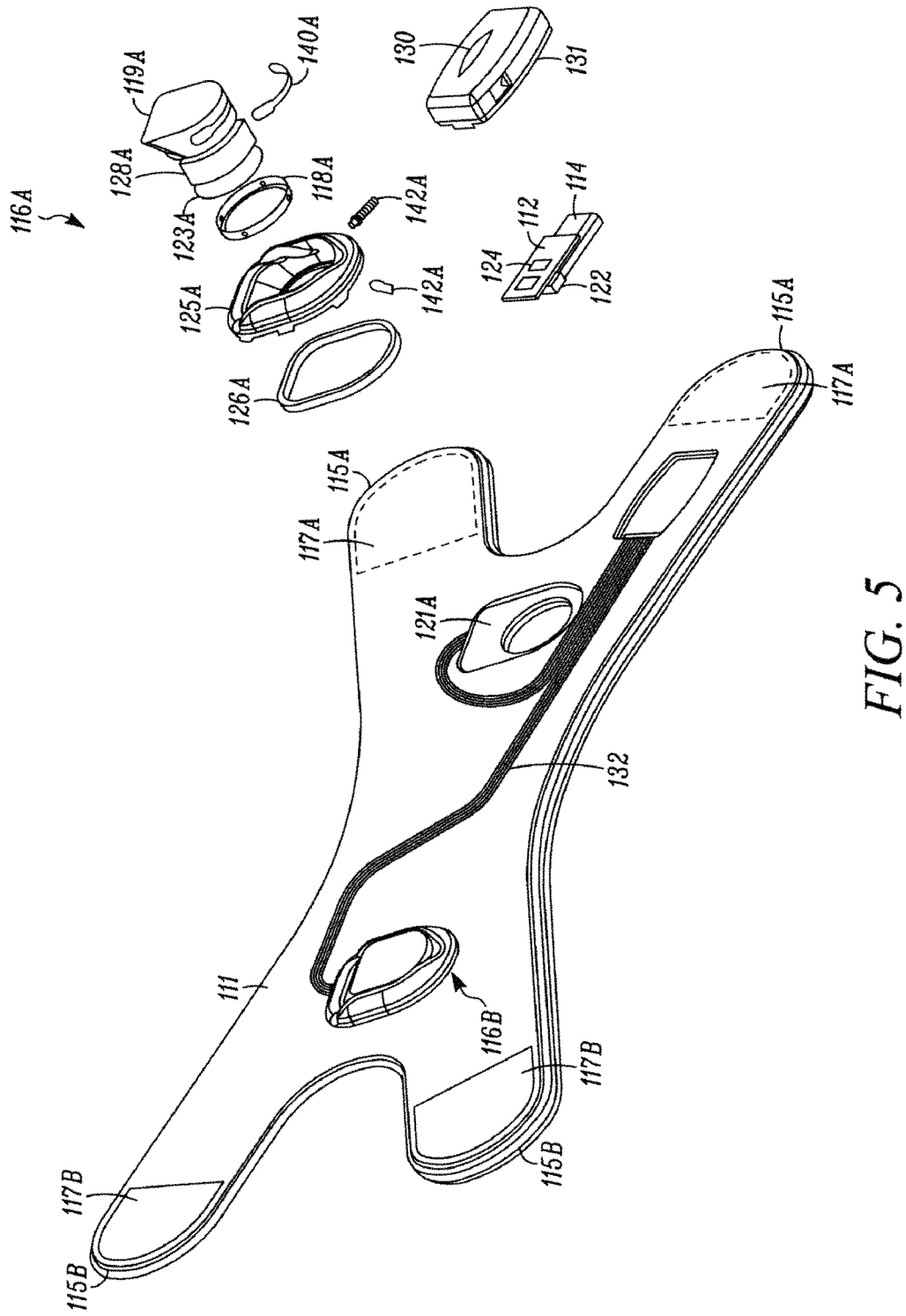
FIG. 5 is an exploded perspective view of the stimulation device of FIG. 3.

FIG. 5 is an exploded perspective view of stimulation device 110 according to a further embodiment. As shown in FIG. 5, first stimulating means 116A includes first coil 126A, first stimulating means holder 125A, first stimulating means holder base plate 121A, first thermal exchange component 128A, and first stimulating means housing 119A. First coil 126A of first stimulating means 116A is designed to be contained within the first stimulating means holder 125A. The first stimulating means holder base plate 121A provides a base for the first stimulating means holder 125A to attach to in order to be joined to the knee cuff by means of any one of such exemplary attachment mechanisms as, but not limited to, an irreversible snap-fit hook mechanism, ultrasonic welding, or glue. In one embodiment, the first stimulating means holder base plate 121A may be permanently attached to the knee cuff 111 by sewing, glue, or any known attachment means. First thermal exchange component 128A is designed to be contained within first thermal stimulating means housing 119A. Housing 119A may then be enclosed on a back side by a thin plastic barrier 123A formed from a material such as Tyvek®. The thin barrier 123A can be attached to the housing 119A by glue, heat seal, or a plastic snap-fit cover 118A. First thermal exchange component 119A is insertable into first stimulating means holder 125A, which is coupled to knee cuff 111 as shown in the embodiment depicted in FIG. 3.

Although not shown in an exploded view like first stimulating means 116A, second stimulating means 116B includes similar components in a similar configuration. Thus, the discussion focuses on first stimulating means 116A for purposes of example only, but applies equally to second stimulating means 116B. As a result, second stimulating means 116B includes similar components having similar reference numerals.

The signal generator 112 depicted schematically in FIG. 5 includes a voltage regulator 122 and a microcontroller 124, which control the signals transmitted through the wire harness 132 to first and second coils 126A and 126B to provide the pulsed electromagnetic field to the knee. The wire harness 132 is hidden within the different fabric layers of the knee cuff 111. Power source 114, which provides power to voltage regulator 122, is positioned in the same housing that contains the signal generator means 112. However, as discussed above, power source 114 may alternatively be positioned remotely from the signal generator means 112. In a further alternative embodiment, two power sources are provided: one for the signal generator and one for the thermal exchange component. In yet another embodiment, three power sources are provided: one for the signal generator and one for each of the thermal exchange components. In one embodiment, the power sources for the thermal exchange components are single-use heating mixtures that provide energy when exposed to air.

First and second coils 126A and 126B are either unipolar or bipolar electromagnets that generate a magnetic field when electrical current flows through them. The magnetic field is created by passing an electric current through first and second coils 126A and 126B, which are preferably formed from a long wire strand coiled around a core. The "pulsed" electromagnetic field may be created by programming microcontroller 124 to turn the electromagnetic field on and off at a rapid rate.

Although first and second thermal exchange components 128A and 128B are not required components, incorporating them into first and second stimulating means 116A and 116B, respectively, may provide beneficial treatment results. In particular, when used in combination with electromagnetic therapy, thermal therapy is helpful in treating the effects of osteoarthritis and improving patient compliance. However, one skilled in the art will appreciate that embodiments of stimulation device 110 that apply only thermal therapy, only electromagnetic therapy, or a combination of both therapies are possible. As a result, the stimulation devices described herein may be tailored to the particular needs of different patients.

Heat is a natural remedy that may be used to both relieve pain and reduce discomfort. This is accomplished by stimulating the patient's thermoreceptors which, in turn, aid in blocking the pain sensation from reaching the brain by relaxing deep muscles to reduce tenderness and pain. In order to attain a therapeutic heat transfer effect including increases in tissue temperature, blood flow, muscle lengthening, and metabolism, an intramuscular temperature of about 104 degrees F. (40 degrees Celsius) must be reached.

Numerous types of heat sources may be utilized to provide beneficial heat therapy in accordance with various implementations. For example, first and second thermal exchange components 128A and 128B may be multi-use cartridges that require the patient to 're-heat' the cartridges before every use, such as by placing the cartridges in the microwave. Alternatively, first and second thermal exchange components 128A and 128B may be one-time use cartridges that are designed to provide an irreversible exothermic reaction to provide a source of heat for a specified amount of time. In one embodiment, first and second thermal exchange components 128A and 128B are cartridges that contain iron, carbon, sodium chloride, sodium thiosulfate, and water. When the CLLHW compound is exposed to air, it undergoes an exothermic reaction that produces heat. In other embodiments, heat may be provided through: a resistive based heating source; selective insulation; or "warmth" radiated from the battery during operation. As will be appreciated by one skilled in the art, first and second thermal exchange components 128A and 128B may be heat sources designed such that they deliver heat therapy for any designated period of time ranging from a few minutes to the entire day. This designated period may or may not coincide with the electromagnetic field duration. In addition, first and second thermal exchange components 128A and 128B may be pulsed such that the heat therapy is not constant.

In one embodiment, power source 114 is a lithium-polymer battery, which may be either a single-use battery or a rechargeable, multi-use battery. If power source 114 is a rechargeable type battery, stimulation device 110 may be configured for attachment to a docking station for recharging the device. Alternatively, the docking station may be designed to receive only power source 114, which may be made removable from stimulation device 110. As one skilled in the art will appreciate, numerous other types of power sources may be used to provide the requisite power to stimulation device 110. For example, stimulation device 110 may be designed to create power from the patient's body movements. Alternatively, stimulation device 110 may be powered through a chemical reaction with heat being the by-product. In this case, the heat by-product may provide the heat therapy to the knee joint.

As shown in FIG. 5, stimulation device 110 further includes display 130 for displaying one or more treatment parameters, such as the treatment mode or the amount of treatment time remaining in a therapy session. Display 130 may utilize many different types of indicator means such as, for example, a light source, a heat-sensitive material that changes color (as a function of elapsed time), a digital timer, or sound repetition. In addition, display 130 may function together with a monitoring means in order to transmit an audio, visual, or tactile-type message to the patient in response to the monitoring means sensing, for example, an electromagnetic field strength that is outside of that defined by the treatment mode. In this instance, display 130 is useful to instruct the patient to remove the stimulation device or to call his or her physician.

Figure 6:
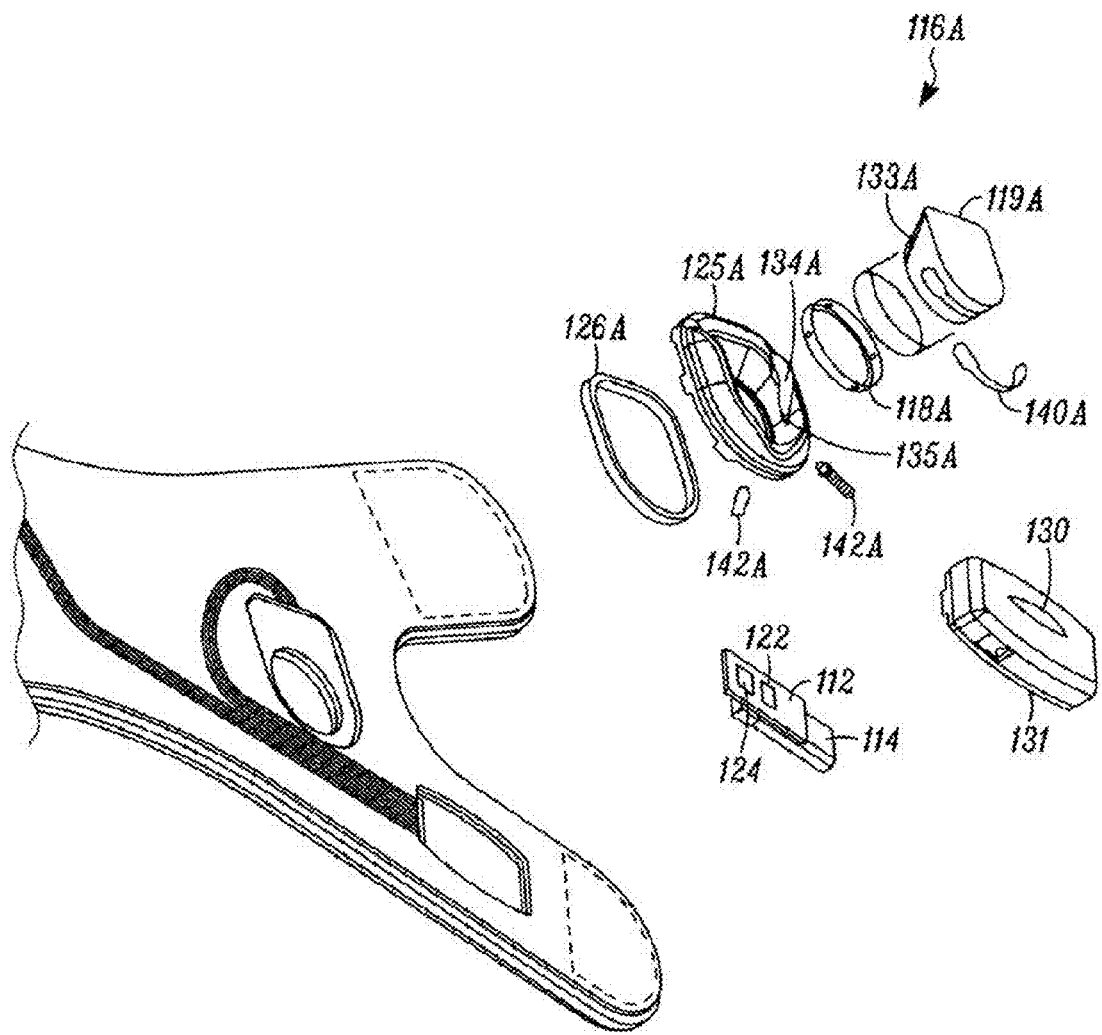
FIG. 6 is an enlarged exploded view of a portion of the stimulation device of FIG. 3.

FIG. 6 is an enlarged illustration of the exploded perspective view of FIG. 5, according to one embodiment. In this embodiment, the stimulating means housings 119A, 119B as depicted in FIG. 5 are insertable, replaceable units that can be easily and quickly inserted into and removed from the means holders 125A, 125B. In one embodiment, the stimulating means housings 119A, 119B have connections that, upon insertion into the holders 125A, 125B, couple with connections in the holders 125A, 125B to supply power to the housings 119A, 119B.

FIG. 6 depicts one embodiment of a stimulation device 110 with insertable stimulating means housings 119A, 119B. As shown in FIG. 6, the stimulation device 110 has a metal plate 140A in the stimulating means housing 119A and a first pair of stimulating means holder spring-loaded metal contacts 142A. When the stimulation device 110 is assembled as shown in the embodiment of FIG. 3, the metal plate 140A on the stimulating means housing 119A is used to make an electrical connection with a pair of spring-loaded metal contacts 142A in the first stimulating means holder 125A. The protrusions 133A on the stimulating means housing 119A can slide in and out of the grooves 134A on the stimulating means holder 125A and engage in the notches 135A to create a reversible mechanical snap-in feature that allows for secure insertion and removal of the housing 119A to the stimulating means holder 125A. In an alternative implementation, the metal plate 140A in the stimulating means housing 119A makes contact with the first pair of stimulating means holder magnets that are inserted into a first pair of magnet notches in first stimulating means holder 125A for securing the housing 119A to the first stimulating means holder 125A. In a further alternative, instead of a metal plate, the stimulation device 110 can have a pair of stimulating means magnets and a corresponding pair of stimulating means holder magnets.

The first pair of stimulating means holder spring-loaded metal contacts 142A are coupled to a corresponding pair of signal lines (not shown) in communication with signal generator 112. When first stimulating means housing 119A is positioned within first stimulating means holder 125A, the electrical connection between the metal plate 140A and the corresponding first pair of stimulating means holder spring-loaded metal contacts 142A creates a closed circuit that electrically couples first stimulating means 116A to signal generator 112. As a result, signal generator 112 is able to communicate with first stimulating means 116A to deliver the prescribed treatment signals defined by the treatment mode programmed into microcontroller 124.

The embodiment of stimulation device 110 illustrated in FIGS. 3-6 is a two coil arrangement with one coil on either side of the knee for generating the PEMF therapy. In general, voltage regulator 122 is used to provide a constant supply voltage to signal generator 112, and first and second stimulating means 116A and 116B. Microcontroller 124 triggers first and second coils 126A and 126B, thereby generating accurate pulses at a particular triggering and switching frequency defined by the designated treatment mode stored in the microcontroller. The triggering frequency is defined as the rate at which a set number of pulses occur. The switching frequency is the fundamental frequency of the individual pulses. Another parameter called the switching duty cycle is defined as the ratio of the pulse width over the switching period. The voltage of the pulses is equivalent to the amplitude of the PEMF therapy.

The required penetration depth of the pulsed electromagnetic field generated by signal generator 112 and first and second stimulating means 116A and 116B may vary depending upon, for example, the size of the patient's knee region. However, for an adult patient, the penetration depth is generally in the range of about 1 cm to about 5 cm. Alternatively, the penetration depth is in the range of about 2 cm to about 4 cm. In a further alternative, the penetration depth ranges from about 2 cm to about 2.5 cm. This "penetration depth" parameter is necessary in order to estimate the magnetic field intensity needed to provide the therapy, which ultimately determines the power requirement of power source 114.

In general, the magnetic field intensity generated by a coil is measured in terms of Tesla (T) and has the following approximate relationship with current flowing through the coil:

$$B = \frac{\mu_0 n I R^2}{2(R^2 + x^2)^{3/2}} \Rightarrow I \frac{2B(R^2 + x^2)^{3/2}}{\mu_0 n R^2}$$

where "B" is the magnetic field produced by the coil, "I" is the current through the coil, "R" is the radius of the coil, and "x" is the penetration depth of the PEMF.

According to one embodiment, the magnetic field strength B applied to the target body part of the patient ranges from about 10 µT to about 2,000 µT. Alternatively, the magnetic field strength B ranges from about 20 µT to about 100 µT. In a further alternative, the magnetic field strength B ranges from about 30 µT to about 50 µT. In yet another alternative, the magnetic field strength B is about 40 µT. According to one embodiment, the magnetic field produced by the coil is applied perpendicular to the coil.

In one implementation, the magnetic field is applied into the knee for a distance ranging from about 1 cm to about 5 cm into the knee. Alternatively, the magnetic field is applied for a distance ranging from about 2 cm to about 4 cm into the knee. In a further alternative, the magnetic field is applied to a distance ranging from about 2 cm to about 2.5 cm into the knee.

The coil, in accordance with one embodiment, has 20 turns of a 24 AWG wire around a core with a radius of about 2 centimeters with a pulsed current 712 mA. Alternatively, the coil has 65 turns of a 28 AWG wire around a core with a radius of 1.5 cm with a pulsed current of 339 mA.

While a single-coil configuration is possible and within the intended scope of this application, the two-coil configuration uses about 20 times less power than the single-coil configuration because it requires a significantly smaller amount of energy to penetrate both the lateral and medial side of the knee. Furthermore, embodiments having more than two coils are also contemplated.

In one embodiment, the PEMF therapy is applied for period ranging from about 30 minutes to about 4 hours. Alternatively, the PEMF therapy is applied for a period ranging from about 1 hour to about 3 hours. In a further alternative, the therapy is applied from about 1.5 to about 2.5 hours. In yet another alternative, the therapy is applied for about 2 hours. Further, the optimal treatment window may vary depending upon many factors, including, but not limited to, the field intensity provided to the knee, the severity of the osteoarthritis in the knee, and the physical dimensions of the knee.

According to one implementation, the triggering frequency ranges from about 1 Hz to about 100 Hz. Alternatively, the triggering frequency ranges from about 5 Hz to about 50 Hz. In a further alternative, the triggering frequency ranges from about 10 Hz to about 20 Hz. In yet another alternative, the triggering frequency is about 15 Hz.

In accordance with one embodiment, the switching frequency ranges from about 50 Hz to about 100 kHz. Alternatively, the switching frequency ranges from about 300 Hz to about 70 kHz. In a further alternative, the switching frequency ranges from about 2 kHz to about 4 kHz. In yet another alternative, the switching frequency is about 3 kHz.

In general, in order to achieve the optimal therapeutic effect with the PEMF, a triggering frequency in the range of about 15 Hz and a switching frequency in the range of about 3 kHz are desirable, although other triggering and switching frequencies are also contemplated.

As one skilled in the art will appreciate based upon the above disclosure, stimulation device 110 does not require connection to any external hardware while delivering the prescribed therapy. Thus, stimulation device 110 is portable, and is designed such that it may be worn by the patient during their normal daily activities without discomfort. Knee cuff 111 may be both ergonomically designed and cosmetically appealing to increase patient compliance with wearing the device.

First and second stimulating means 116A and 116B may be designed as complete or partial disposable units that may be discarded and replaced after a predetermined number of treatments. For example, stimulating means housing 119A, which may include first thermal exchange component 128A and/or first coil 126A, may be removed from stimulation means holder 125A and disposed of by the patient upon expiration. Optionally, display 130 may instruct the patient when the units have expired and require replacement. The disposability feature of first and second stimulating means 116A and 116B may be advantageous because if one or more of the stimulating means stops functioning properly, it is only necessary to replace those components and not the entire stimulation device.

Figure 7:
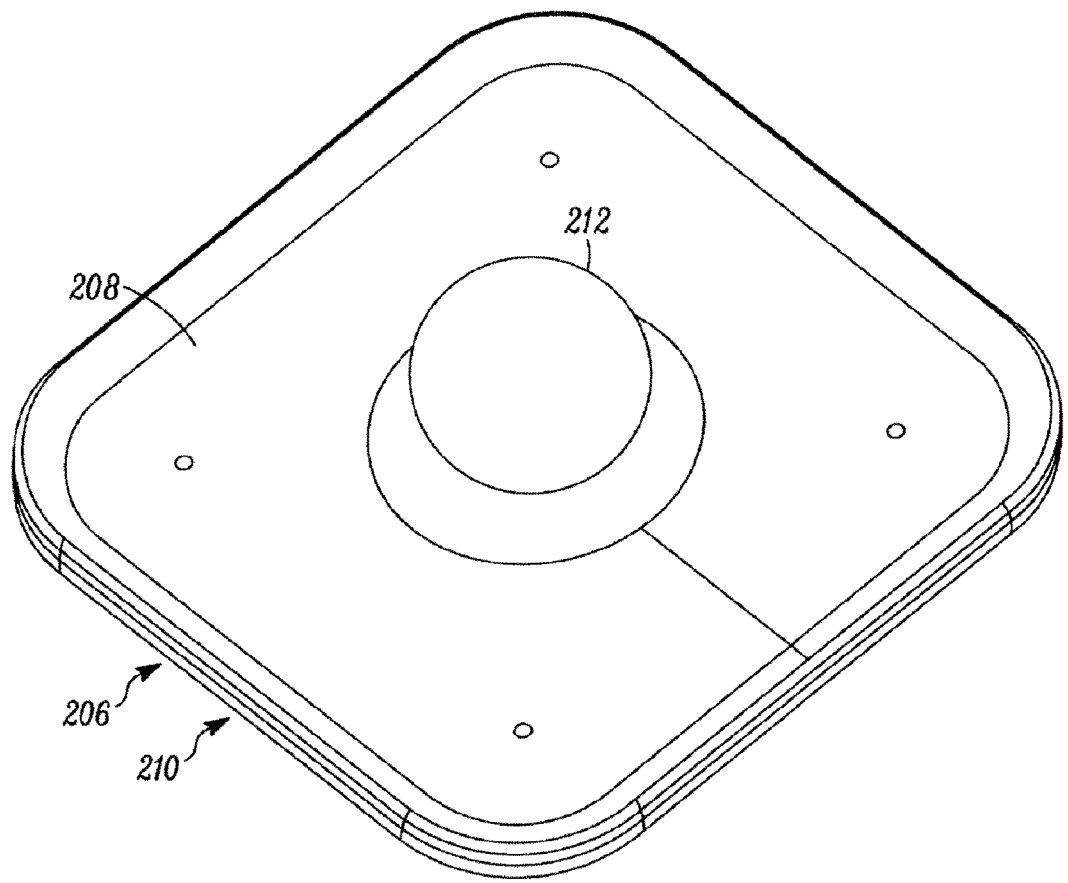
FIG. 7 is a perspective view of one embodiment of a stimulation device in the form of a patch that is securable to a patient's body for delivery of electromagnetic and thermal therapy.

Another exemplary embodiment of an $EMT^2$ stimulation device is depicted in FIG. 7. The device 200 shown in FIG. 7 has a PEMF generation component 202 and a thermal exchange component 204. The PEMF generation component 202 is positioned between a first exterior layer 206 and a second exterior layer 208. According to one embodiment, the first layer 206 has an adhesive component 210 on at least a portion of the side of the layer external to the device 200. The adhesive component 210 is any known adhesive that allows for attaching the device 200 to the patient's skin.

In accordance with one implementation, the device 200 also has a power source (not shown) positioned in an external casing 212 positioned on the second layer 208. In a further embodiment, certain electronic components can be positioned in the casing 212.

Alternatively, the device 200 has two power sources (not shown)—one for the PEMF generation component 202 and one for the thermal exchange component 204. Two different power sources can help to maximize battery life. Alternatively, one power source is provided for both the PEMF generation component 202 and the thermal exchange component 204. In a further embodiment, one power source is provided for the PEMF generation component 202, and the thermal exchange component 204 in this embodiment requires no power source, as explained in further detail below. According to one implementation, the single power source or both power sources are positioned in the external casing 212. Alternatively, the single power source or both power sources are positioned between the first layer 206 and the second layer 208. In a further alternative, one power source is positioned in the external casing 212 and one power source is positioned in between the first 206 and second 208 layers.

In one embodiment, one or both of the power sources are a single-use or disposable power source. Alternatively, the one or more power sources can be reusable or permanent power sources. In a further alternative, the power source is any known power source for use with a PEMF stimulation device and/or a thermal exchange component.

In one embodiment, the device 200 is a single-use patch-like device. Alternatively, the device 200 is a reusable device. As shown, the device 200 has a square shape. Alternatively, the device 200 can have a circular or round shape or any other known shape. For example, in one embodiment, the device 200 may have any shape that maximizes attachment to the patient's skin and patient comfort.

In this embodiment, the PEMF generation component 202 is a coil configured to generate the pulsed electromagnetic field. Alternatively, the PEMF generation component 202 can be any known component for generating a PEMF.

According to one implementation, the thermal exchange component 204 is a heat source such as, for example, a component having an exothermic chemical mixture. For example, the heat source in one embodiment is a mixture containing iron powder, water, activated charcoal, and salt that oxidizes in air to generate heat. One commercial example of such a mixture can be found in hand warming products sold by HeatMax®, which is located in Dalton, Ga. Another example of a heat source that can be used with the present embodiment is a mixture containing super-cooled sodium acetate. Yet another example is a mixture containing calcium chloride or magnesium sulfate and water. In a further alternative, the thermal exchange component can be any known component or device for generating heat.

In accordance with one implementation in which the thermal exchange component 204 is a heat source utilizing an exothermic chemical mixture, the component 204 does not require a power source. That is, the chemical mixture generates the exothermic reaction without the need for any battery or any other kind of power source.

Alternatively, the thermal exchange component 204 is a cooling source such as, for example, a component having an endothermic chemical mixture. For example, the cooling source can be a mixture containing ammonium nitrate and water. In a further alternative, the thermal exchange component 204 can be any known component for providing a temperature reduction.

In one implementation, the first and second exterior layers 206, 208 are flexible or pliable layers. The layer pliability or flexibility can, according to one embodiment, facilitate attachment of the device 200 to the patient's skin. In one alternative embodiment, one or both of the exterior layers can be gas permeable. In a further alternative, one or both of the exterior layers are permeable to oxygen. The layers 206, 208 can consist of a biocompatible membrane such as, for example, the Tegaderm™ and Medipore™ products available from 3M™ Company, located in St. Paul, Minn.

According to one embodiment, the adhesive component 210 is a hypoallergenic adhesive. In a further alternative implementation in which one or both of the exterior layers 206, 208 are gas permeable, the adhesive component 210 is a porous adhesive that allows gas to pass through the adhesive and the gas permeable layer.

It is understood that this device 200 can be used to treat any joint or any other body part that might benefit from treatment with PEMF and thermal exchange. In one embodiment, the target area is the knee. It is further understood that more than one device 200 could be used to treat a target area. The device 200 can be used to relieve osteoarthritis pain and increase range of motion.

One skilled in the art will appreciate that although the devices and methods have been described in reference to only a few embodiments of a stimulation device, these embodiments are provided for purposes of example and not limitation. Accordingly, numerous other embodiments are possible and within the intended scope.

Other Examples

Figure 8:
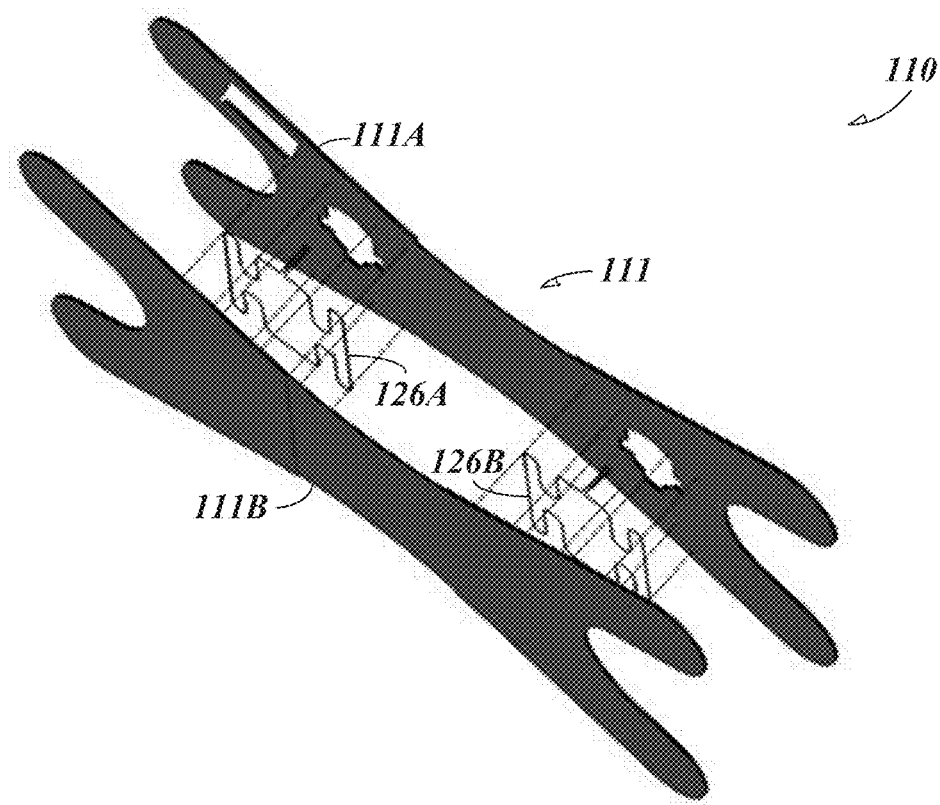
FIG. 8 illustrates generally an exploded perspective view of an active knee system.

FIG. 8 illustrates generally an example of an active knee system including a stimulation device 110, the stimulation device 110 including a knee cuff 111 having a first layer 111A and a second layer 111B. In the example of FIG. 8, the active knee system includes a portable, battery operated, non-invasive shortwave diathermy medical device that applies electromagnetic energy for the treatment of medical conditions using means other than the generation of deep heat within body tissues (e.g., using athermal means).

In an example, the active knee system can be configured to deliver a pulsed RF signal to a target tissue via inductive coupling with applicator coils (e.g., a first coil 126A and a second coil 126B). In this example, the applicator coils are placed on either side of a knee (e.g., the medial and lateral areas of the knee joint) within the knee cuff 111 (e.g., between the first layer 111A and the second layer 111B). In other examples, the applicator coils can be placed in other locations about the knee cuff (e.g., depending on the desired target tissue) or one or more applicator coils can be placed in one or more locations within one or more other cuffs configured to be placed about one or more other parts of the body.

In an example, separate RF signal generators can be located proximate each applicator coil (e.g., within a stimulation means holder, proximate an applicator coil, or in certain examples, within the same sub-assembly as the applicator coil) to significantly reduce potential RF signal degradation in comparison to a system having multiple applicator coils separately routed, in some examples, substantially large distances, to a single RF signal generator. In other examples, separate RF signal generators can be assigned to a first group of applicator coils located in closer proximity than a second group of applicator coils.

In certain examples, one or more of the RF signal generators or the applicator coils can be controlled by a single microcontroller contained within a separate housing (e.g., a housing 131) removable from the knee cuff 111 (or one or more other cuff). The microcontroller can control the RF signal generators (e.g., on-state, off-state, etc.) using a low-speed power line. The combination of the RF signal generators located proximate the applicator coils and the separate microcontroller can allow complete modularization of the system (e.g., the one or more RF signal generators or applicator coils can be placed independently from the microcontroller).

The stimulation device 110 can include one or more disposable, single-use, air activated pods that provide heat or cold to a target tissue. In an example, the one or more pods can be snapped or otherwise attached into medial and lateral slots or holders on the knee cuff 111. In various examples, treatment (e.g., PEMF therapy, or one or more of thermal therapy or electromagnetic therapy) can occur through dressings, clothing, casts, compression garments, supports, or one or more other barrier between the knee cuff 111 and the target tissue. Further, in certain examples, the pods (separately or in combination) can act as an activator switch that enables or turns on one or more portion of the PEMF therapy.

In an example, the PEMF therapy can include one or more of the following parameters: 1 W peak generator power; 4 mW average generator power; 3V generator voltage; a voltage standing wave ration of approximately 1; 10 mA current; 27.12 MHz carrier frequency; 2 msec burst duration (e.g., 2 msec burst on, and 498 msec burst off); 2 Hz burst frequency; 50 Ohm standard load; etc. In other examples, the PEMF therapy can include one or more other parameters.

Although the example of FIG. 8 illustrates generally an active knee system, one or more other systems configured to provide therapy to one or more other target areas are consistent with the teachings herein, such as an active ankle system, an active wrist system, etc.

Active Ankle System

Figure 9:
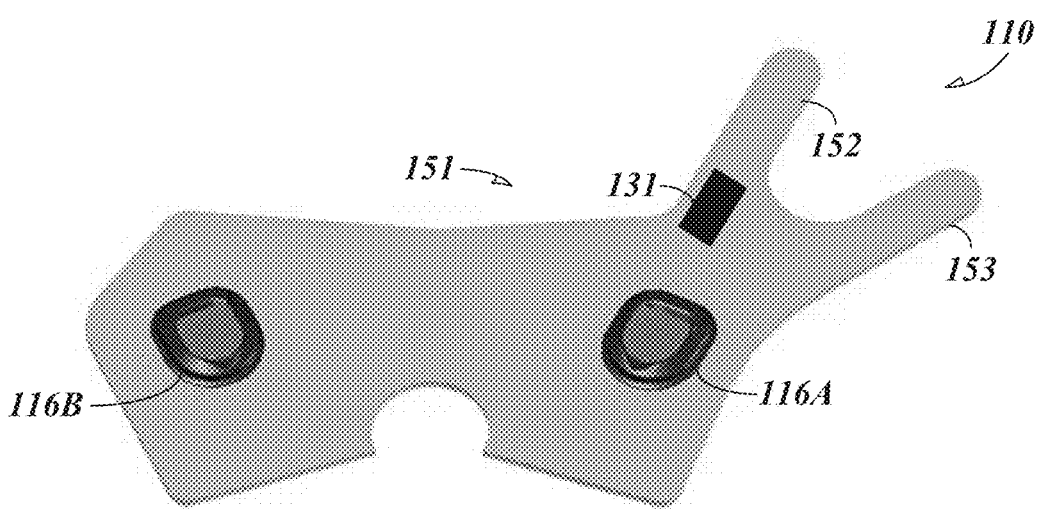
FIG. 9 illustrates generally an example of an active ankle system.

FIG. 9 illustrates generally an example of an active ankle system including a stimulation device 110, the stimulation device 110 including an ankle cuff 151 configured to be worn around an ankle, first and second stimulating means 116A, 116B configured to provide therapy to the ankle, and a housing 131 configured to store a microcontroller to control at least a portion of at least one of the first or second stimulating means 116A, 116B. In an example, the ankle cuff 151 can include fasteners, in this example, first and second straps 152, 153 configured to cross over the front of the ankle and securely fasten the ankle cuff 151 to the ankle. In an example, the fasteners can include hook and loop fasteners, or one or more other type of fastener.

The active ankle system can be configured to deliver PEMF therapy (e.g., a pulsed RF signal) to a target tissue using one or more applicator coils (e.g., first and second coils), as well as thermal therapy (e.g., heat therapy) using one or more disposable, single-use air activated pods, to a target area of the ankle. In an example, the first or second stimulating means 116A, 116B can include at least one of an applicator coil or a thermal pod. In an example, the PEMF or thermal therapies can be provided near the tibiotalar and talocalcaneal joints of the ankle, which are generally the most common places for arthritis in the ankle to occur. By positioning the applicator coils or the thermal pods at or near the tibiotalar and talocalcaneal joints of the ankle, treatment of both the commonly injured (e.g., when an ankle is rolled or sprained) posterior and anterior talo-fibular ligaments is possible.

In other examples, the PEMF or thermal therapies can be used to reduce post-surgical pain and edema in the ankle, as well as provide one or more other therapeutic benefits. Using the unique wrap design illustrated in FIG. 9, the ankle cuff 151 can be worn on either the left or right ankle and still provide therapy to the target locations of the ankle without producing different active ankle systems for each side. Further, the applicator coils or the thermal pods can be placed in one or more other locations about the ankle cuff 151 due to the modular design of the system, such as described above.

Active Back System

Figure 10:
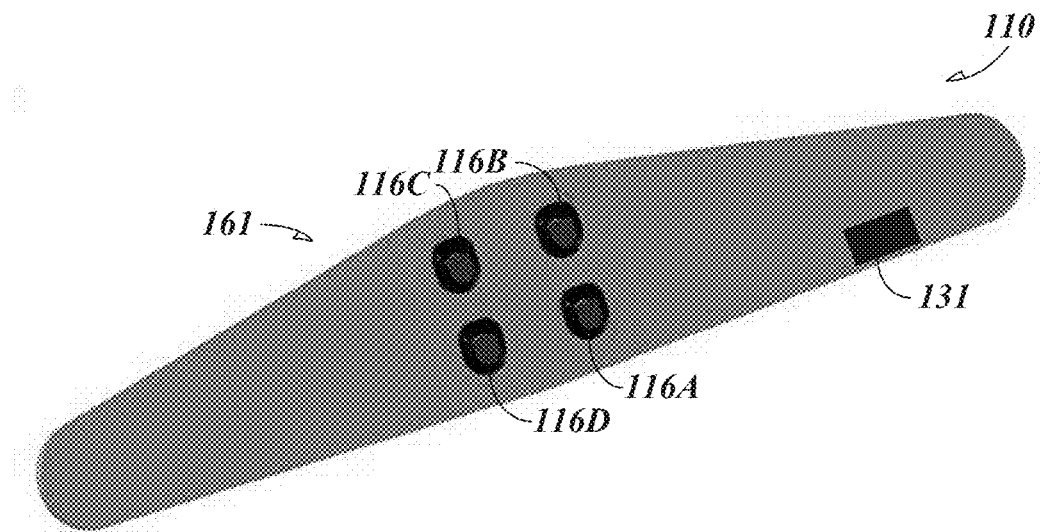
FIG. 10 illustrates generally an example of an active back system.

FIG. 10 illustrates generally an example of an active back system including a stimulation device 110, the stimulation device 110 including a back wrap 161 configured to be worn around a back, stimulating means (e.g., first, second, third, and fourth stimulating means 116A, 116B, 116C, 116D, respectively) configured to provide therapy to the back, and a housing 131 configured to store a microcontroller configured to control at least a portion of at least one of the first, second, third, or fourth stimulating means 116A, 116B, 116C, 116D. In an example, the back wrap 161 can be positioned in place securely about the back using fasteners, such as hook and loop fasteners located at opposite ends of the back wrap 161.

In an example, the active back system can be configured to deliver PEMF therapy (e.g., a pulsed RF signal) to a target tissue using one or more applicator coils (e.g., first and second applicator coils, or any other number of applicator coils), as well as thermal therapy (e.g., heat therapy) using one or more disposable, single-use air activated pods, to a target area of the back. In certain examples, the first through fourth stimulating means 116A, 116B, 116C, 116D, can include at least one of an applicator coil or a thermal pod. In an example, the PEMF or thermal therapies can be provided on one or more sides of the spine, in one or more areas of pain due to various reasons (e.g., surgery, arthritis, poor posture, etc.), such as the lumbar region of the back.

In an example, to reduce cost, but still provide therapy to the subject, a sub-set of stimulating means can include both the applicator coil and the thermal pod, while others include only a thermal pod (e.g., the lower stimulating means including applicator coils and thermal pods, and the upper stimulating means including only thermal pods, etc.). Further, the applicator coils or the thermal pods can be placed in one or more other locations about the back wrap 161 due to the modular design of the system, such as described above.

Active Elbow System

Figure 11:
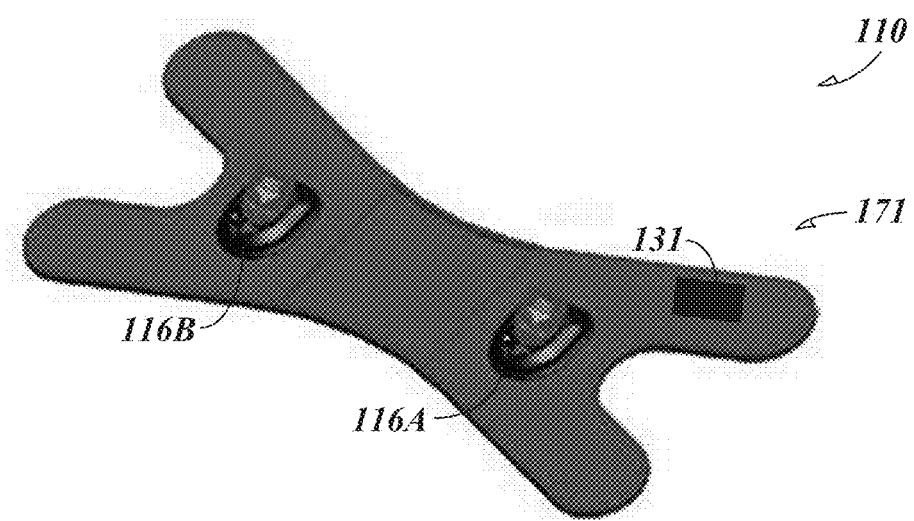
FIG. 11 illustrates generally an example of an active elbow system.

FIG. 11 illustrates generally an example of an active elbow system including a stimulation device 110, the stimulation device 110 including an elbow cuff 171 configured to be worn around an elbow, first and second stimulating means 116A, 116B configured to provide therapy to the elbow, and a housing 131 configured to store a microcontroller configured to control at least a portion of at least one of the first or second stimulating means 116A, 116B. In an example, the elbow cuff 171 can be worn around the elbow, secured in place by fasteners (e.g., hook and loop fasteners located at ends of the elbow cuff 171) in a similar fashion as the active knee system is secured around the knee.

In an example, the first or second stimulating means 116A, 116B can include at least one of an applicator coil or a thermal pod. In an example, the PEMF and thermal therapies can be provided near the medial and lateral sides of the elbow, in certain examples, providing treatment over the lateral epicondyle to treat one or more injuries or condition, such as tennis elbow, etc.

In other examples, the PEMF and thermal therapies can be used to reduce post-surgical pain and edema in the elbow, as well as provide one or more other therapeutic benefits. Using the unique wrap design illustrated in FIG. 11, the elbow cuff 171 can be worn on either the left or right elbow and still provide therapy to the target locations of the elbow without producing different active elbow systems for each side. Further, the applicator coils or the thermal pods can be placed in one or more other locations about the elbow cuff 171 due to the modular design of the system, such as described above.

Active Wrist System

Figure 12:
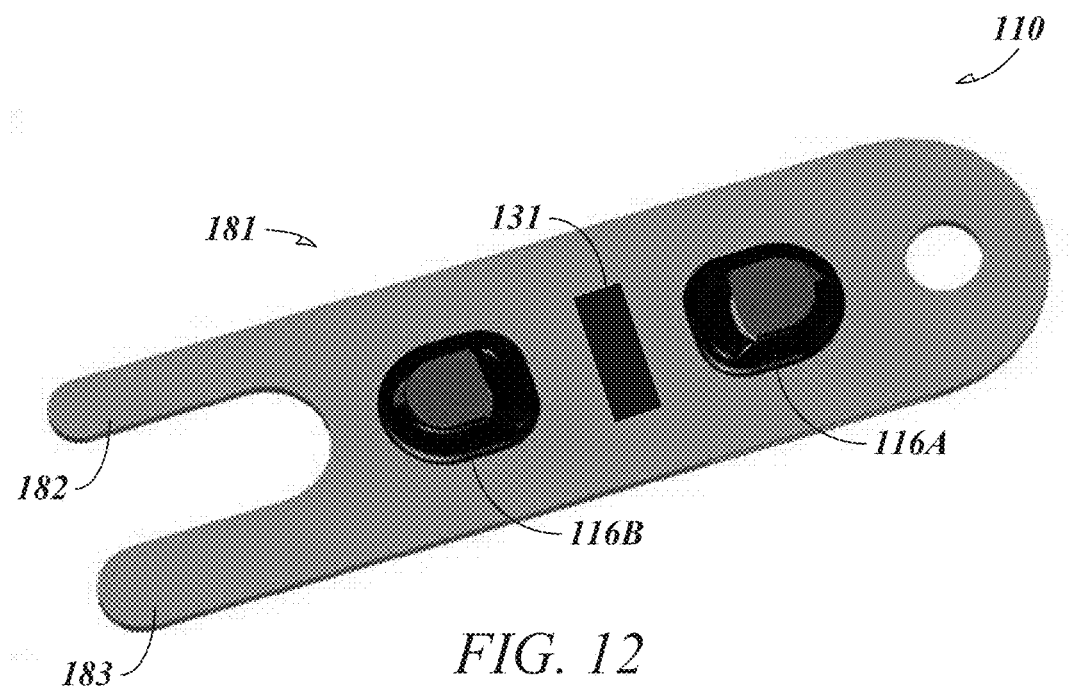
FIGS. 12 and 13 illustrate generally examples of an active wrist system.

FIG. 12 illustrates generally an example of an active wrist system including a stimulation device 110, the stimulation device 110 including a wrist cuff 181 configured to be worn around a wrist, first and second stimulating means 116A, 116B configured to provide therapy to the wrist, and a housing 131 configured to store a microcontroller configured to control at least a portion of at least one of the first or second stimulating means 116A, 116B. In an example, the wrist cuff 181 can be worn by placing the thumb through the hole in the wrist cuff 181 and wrapping the wrist cuff 181 around the wrist. In an example, the wrist cuff 181 can include fasteners, in this example, first and second straps 182, 183. In an example, the fasteners can include hook and loop fasteners, or one or more other type of fastener.

In an example, the first or second stimulating means 116A, 116B can include at least one of an applicator coil or a thermal pod. In an example, the PEMF and thermal therapies can be provided near the medial and lateral areas of the wrist, in certain examples, providing treatment at or near the basal joint, a common location of arthritis. Further, by positioning the applicator coils or the thermal pods at or near the basal joint, treatment over the two collateral ligaments in the wrist is possible.

In other examples, the PEMF or thermal therapies can be used to reduce post-surgical pain and edema in the wrist, as well as provide one or more other therapeutic benefits. Using the unique wrap design illustrated in FIG. 12, the wrist cuff 181 can be worn on either the left or right wrist and still provide therapy to the target locations of the wrist without producing different active wrist systems for each side. Further, the applicator coils or the thermal pods can be placed in one or more other locations about the wrist cuff 181 due to the modular design of the system, such as described above.

Figure 13:
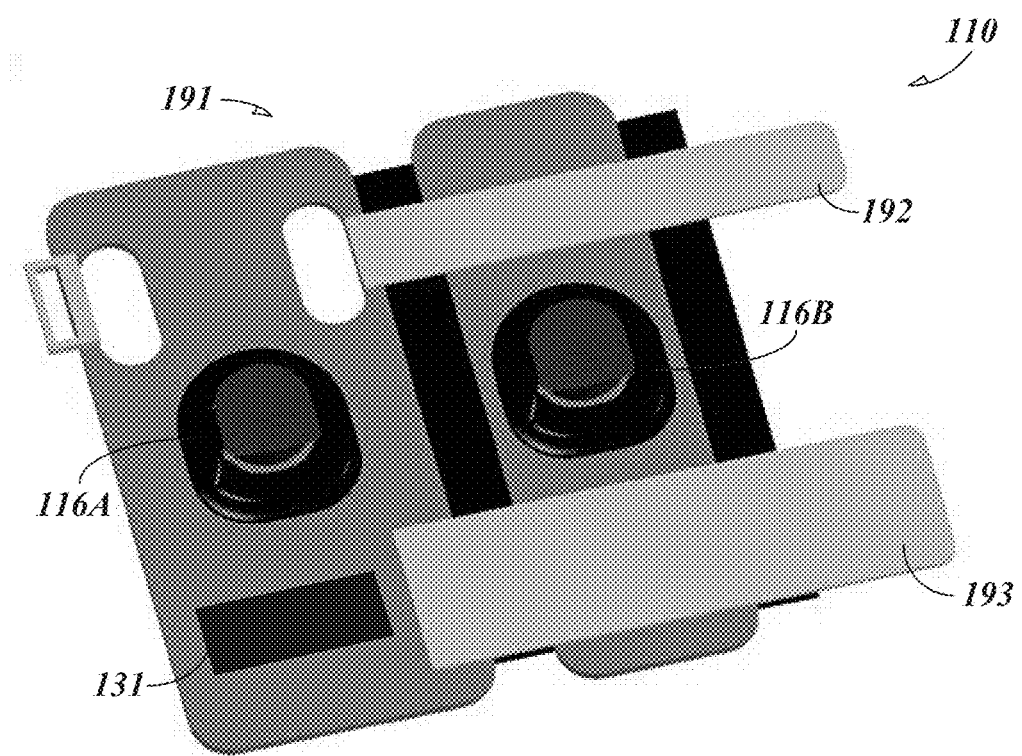

FIG. 13 illustrates generally an example of an active wrist system including a stimulation device 110, the stimulation device 110 including a wrist cuff 191 configured to be worn around a wrist, first and second stimulating means 116A, 116B configured to provide therapy to the wrist, and a housing 131 configured to store a microcontroller configured to control at least a portion of at least one of the first or second stimulating means 116A, 116B. In this example, the thumb can be pushed through the appropriate thumb hole and first and second straps 192, 193 can be adjusted to secure the wrist cuff 191 in place using fasteners, such as hook and loop fasteners, or one or more other fasteners. In an example, the wrist cuff 191 can secure the stimulation first and second stimulating means 116A, 116B over the center of the wrist, allowing the therapy to penetrate deep within the wrist.

In other examples, the PEMF or thermal therapies can be used to reduce post-surgical pain and edema in the wrist, as well as provide one or more other therapeutic benefits. Using the unique wrap design illustrated in FIG. 13, the wrist cuff 191 can be worn on either the left or right wrist and still provide therapy to the target locations of the wrist without producing different active wrist systems for each side. Further, the applicator coils or the thermal pods can be placed in one or more other locations about the wrist cuff 191 due to the modular design of the system, such as described above.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A portable, non-invasive device for providing therapeutic treatment to a joint to promote healing of the joint, the device comprising:
    a cuff positionable around the joint, the cuff including:
        an electromagnetic stimulator configured to receive a signal from a signal generator and to provide an electromagnetic field within the joint using the received signal; and
        a single-use thermal exchange component removably coupled to the cuff and configured to provide temperature-based therapy to the joint;
    a receptacle coupled to the cuff proximate the electromagnetic stimulator; and
    a disposable housing including the single-use thermal exchange component, wherein the disposable housing is configured to be mechanically coupled to the receptacle;
    wherein the disposable housing, when mechanically coupled to the receptacle, is configured to enable the electromagnetic stimulator to generate the electromagnetic field within the joint.

2. The device of claim 1, wherein the electromagnetic stimulator includes a coil configured to provide the electromagnetic field within the joint.

3. The device of claim 2, including the signal generator, wherein the signal generator is configured to generate pulsed signals; and
    wherein the coil is configured to receive the pulsed signals from the signal generator and to provide a pulsed electromagnetic field within the joint.

4. The device of claim 1, wherein the electromagnetic stimulator includes a medial coil configured to provide the electromagnetic field within a medial area of the joint and a lateral coil configured to provide the electromagnetic field within a lateral area of the joint.

5. The device of claim 1, wherein the single-use thermal exchange component includes a medial single-use thermal exchange component configured to provide temperature-based therapy to a medial area of the joint and a lateral single-use thermal exchange component configured to provide temperature-based therapy to a lateral area of the joint.

6. The device of claim 1, wherein the single-use thermal exchange component includes a heat source configured to provide heat therapy to the joint.

7. The device of claim 6, wherein the heat source includes a heating mixture configured to undergo an exothermic reaction that produces heat when exposed to air.

8. The device of claim 1, wherein the single-use thermal exchange component includes a cooling source configured to provide cooling therapy to the joint.

9. The device of claim 8, wherein the cooling source includes a mixture configured to undergo an endothermic reaction.

10. The device of claim 1, wherein the electromagnetic stimulator is configured to generate the electromagnetic field within the joint that coincides in duration with the temperature-based therapy to the joint.

11. A method for providing therapeutic treatment to a joint, the method comprising:
    providing a cuff positionable around the joint, the cuff including:
        an electromagnetic stimulator configured to provide an electromagnetic field within the joint; and
        a single-use thermal exchange component removably coupled to the cuff and configured to provide temperature-based therapy to the joint;
    receiving, using the electromagnetic stimulator, a signal from a signal from a signal generator;
    generating, using the electromagnetic stimulator, an electromagnetic field within the joint using the received signal; and
    providing temperature-based therapy to the joint using the single-use thermal exchange component;
    containing the single-use thermal exchange component in a disposable housing configured to be removably mechanically coupled to a receptacle on the cuff; and
    wherein removably mechanically coupling the disposable housing to the receptacle on the cuff is configured to enable the generating the electromagnetic field within the joint.

12. The method of claim 11, wherein the generating the electromagnetic field within the joint includes using a coil.

13. The method of claim 11, wherein the generating the electromagnetic field within the joint includes generating a pulsed electromagnetic field within the joint.

14. The method of claim 11, wherein the generating the electromagnetic field within the joint includes generating an electromagnetic field within a medial area of the joint using a medial coil and generating an electromagnetic field within a lateral area of the joint using a lateral coil.

15. The method of claim 11, wherein the providing the temperature-based therapy to the joint includes providing temperature-based therapy to a medial area of the joint using a medial single-use thermal exchange component and providing temperature-based therapy to a lateral area of the joint using a lateral single-use thermal exchange component.

16. The method of claim 11, wherein the providing the temperature-based therapy to the joint includes providing heat therapy to the joint.

17. The method of claim 11, wherein the providing the temperature-based therapy to the joint includes providing cooling therapy to the joint.

* * * * *

UNITED STATES PATENT AND TRADEMARK OFFICE
CERTIFICATE OF CORRECTION

PATENT NO. : 8,768,454 B2  Page 1 of 1
APPLICATION NO. : 12/831779
DATED : July 1, 2014
INVENTOR(S) : Sham et al.

It is certified that error appears in the above-identified patent and that said Letters Patent is hereby corrected as shown below:

In the Claims

Column 20, line 22, in Claim 11, before "from", delete "from a signal", therefor Signed and Sealed this
Eleventh Day of November, 2014

Michelle K. Lee
*Deputy Director of the United States Patent and Trademark Office*